(12) United States Patent
Fukunaga

(10) Patent No.: US 10,602,919 B2
(45) Date of Patent: Mar. 31, 2020

(54) IMAGING DEVICE

(71) Applicant: OLYMPUS CORPORATION, Hachioji-shi, Tokyo (JP)

(72) Inventor: Yasuhiro Fukunaga, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 235 days.

(21) Appl. No.: 15/797,469

(22) Filed: Oct. 30, 2017

(65) Prior Publication Data
US 2018/0049633 A1  Feb. 22, 2018

Related U.S. Application Data

(63) Continuation of application No. PCT/JP2015/063073, filed on May 1, 2015.

(51) Int. Cl.
*A61B 1/06* (2006.01)
*H01L 27/146* (2006.01)
(Continued)

(52) U.S. Cl.
CPC .............. *A61B 1/0638* (2013.01); *A61B 1/04* (2013.01); *A61B 5/02* (2013.01); *H01L 27/14621* (2013.01); *H01L 27/14634* (2013.01); *H01L 27/14645* (2013.01); *H01L 27/14647* (2013.01); *H04N 5/2256* (2013.01); *H04N 5/3696* (2013.01); *H04N 9/045* (2013.01); *H04N 9/64* (2013.01); *H01L 27/14636* (2013.01);
(Continued)

(58) Field of Classification Search
USPC ....................................................... 348/68
See application file for complete search history.

(56) References Cited

U.S. PATENT DOCUMENTS

2014/0084404 A1  3/2014  Fukunaga
2014/0194748 A1  7/2014  Yamamoto et al.

FOREIGN PATENT DOCUMENTS

EP  2117047 A1  11/2009
JP  2006-297093 A  11/2006
(Continued)

OTHER PUBLICATIONS

International Search Report dated Jul. 21, 2015, issued in counterpart application No. PCT/JP2015/063073, w/English translation. (2 pages).

*Primary Examiner* — James M Anderson, II
(74) *Attorney, Agent, or Firm* — Westerman, Hattori, Daniels & Adrian, LLP

(57) ABSTRACT

An imaging device includes a first substrate including a plurality of first pixels and a plurality of second pixels, a second substrate including a plurality of third pixels and facing the first substrate, and a processing unit. The plurality of third pixels receive light transmitted through the plurality of first pixels. The plurality of first pixels output signals corresponding to a wavelength bandwidth including wavelengths of green light and transmit a wavelength bandwidth including wavelengths of red light. The plurality of second pixels output signals corresponding to a wavelength bandwidth including wavelengths of blue light and not including wavelengths of red light and wavelengths of green light. The plurality of third pixels output signals corresponding to a wavelength bandwidth including wavelengths of red light. The processing unit generates a signal at least from an output of the plurality of first pixels and an output of the plurality of third pixels.

7 Claims, 11 Drawing Sheets

(51) Int. Cl.
*H04N 9/04* (2006.01)
*A61B 1/04* (2006.01)
*A61B 5/02* (2006.01)
*H04N 5/225* (2006.01)
*H04N 5/369* (2011.01)
*H04N 9/64* (2006.01)

(52) U.S. Cl.
CPC ............ *H04N 2005/2255* (2013.01); *H04N 2209/047* (2013.01)

(56) References Cited

FOREIGN PATENT DOCUMENTS

| | | |
|---|---|---|
| JP | 2009-272620 A | 11/2009 |
| JP | 2014-64196 A | 4/2014 |
| JP | 2014-135535 A | 7/2014 |

IMAGING DEVICE

This application is a continuation application based on a PCT International Application No. PCT/2015/063073, filed on May 1, 2015. The content of the PCT International Application is incorporated herein by reference.

BACKGROUND OF THE INVENTION

Field of the Invention

The present invention relates to an imaging device.

Description of Related Art

In narrow-band imaging (NBI), an image is captured by emitting narrow-band light. Capillary vessels and mucosal microscopic patterns on a mucosal surface layer are highlighted by performing emphasis processing mainly using signals of B pixels (pixels provided to detect blue light) among pixels included in an image sensor. It is known that it is possible to obtain information on blood vessels in the surface layer and it is effective for observation of cancer and the like.

Using an image sensor with an RGB Bayer array, which is common for NBI imaging, cannot secure a sufficient resolution because there is only one B pixel per four pixels. Thus, an image sensor with a different pixel array from the RGB Bayer array such that the proportion of G pixels in the pixels of the image sensor of the RGB Bayer array is one pixel in every four and the proportion of B pixels is two pixels in every four is known (for example, refer to Japanese Unexamined Patent Application, First Publication No. 2006-297093).

FIG. 15 is a schematic diagram showing a pixel array of an image sensor known in the art in which the proportion of G pixels in the pixels of an image sensor having an RGB Bayer array is one pixel in every four and the proportion of B pixels is two pixels in every four. In the shown example, G pixels 2001 and B pixels 2002 are alternately arranged in odd-numbered rows of the image sensor 2000. B pixels 2002 and R pixels 2003 are alternately arranged in even-numbered rows of the image sensor 2000.

SUMMARY OF THE INVENTION

According to a first aspect of the present invention, an imaging device includes a first substrate including a plurality of first pixels and a plurality of second pixels, a second substrate including a plurality of third pixels, the second substrate facing the first substrate, and a processing unit configured to generate a signal, wherein the plurality of third pixels are configured to receive light transmitted through the plurality of first pixels, wherein the plurality of first pixels are configured to output signals corresponding to a wavelength bandwidth including wavelengths of green light and the plurality of first pixels are configured to transmit a wavelength bandwidth including wavelengths of red light, wherein the plurality of second pixels are configured to output signals corresponding to a wavelength bandwidth including wavelengths of blue light and not including wavelengths of red light and wavelengths of green light, wherein the plurality of third pixels are configured to output signals corresponding to a wavelength bandwidth including wavelengths of red light, wherein the plurality of first pixels and the plurality of second pixels correspond to each other, and wherein the processing unit is configured to generate a signal at least from an output of the plurality of first pixels and an output of the plurality of third pixels, the signal corresponding to a wavelength bandwidth including wavelengths of green light and not including wavelengths of blue light and wavelengths of red light.

According to a second aspect of the present invention, in the imaging device according to the first aspect, a plurality of circuit regions may be arranged in regions corresponding to the plurality of second pixels, and the plurality of circuit regions may be configured to perform at least reading of the plurality of third pixels.

According to a third aspect of the present invention, in the imaging device according to the second aspect, the plurality of circuit regions may be configured to perform reading of the plurality of first pixels and the plurality of second pixels.

According to a fourth aspect of the present invention, in the imaging device according to the first aspect, the plurality of first pixels may be configured to output signals corresponding to a wavelength bandwidth including wavelengths of green light and wavelengths of blue light.

According to a fifth aspect of the present invention, in the imaging device according to the first aspect, the plurality of first pixels may be configured to output signals corresponding to a wavelength bandwidth including wavelengths of green light and not including wavelengths of blue light.

According to a sixth aspect of the present invention, in the imaging device according to the first aspect, the imaging device may be configured to emit narrow-band light to highlight capillary vessels in a mucosal surface layer for observing the capillary vessels, the processing unit may generate a first image from signals output from the plurality of first pixels and the plurality of second pixels included in the first substrate, and the processing unit may generate a second image from signals output from the plurality of third pixels included in the second substrate.

DETAILED DESCRIPTION OF THE INVENTION

Embodiments of the present invention will now be described with reference to the drawings.

First Embodiment

Figure 1:
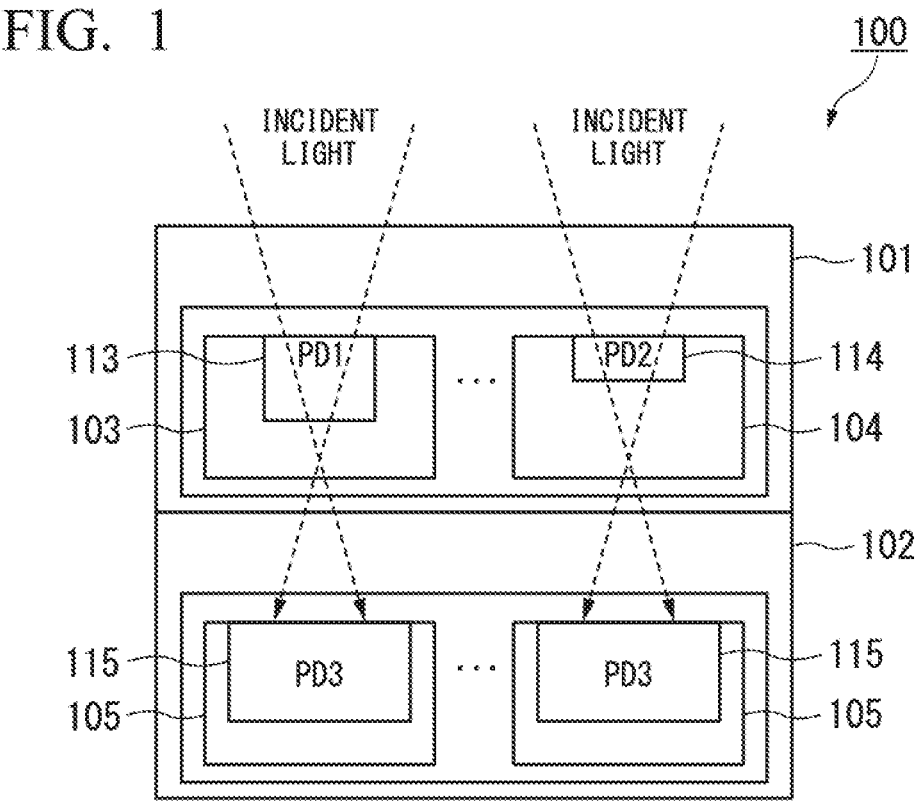
FIG. 1 is a cross-sectional view showing a cross section of an imaging element according to a first embodiment of the present invention.

FIG. 1 is a cross-sectional view showing a cross section of an imaging element 100 according to a first embodiment of the present invention. In the shown example, the imaging element 100 includes a first substrate 101, a second substrate 102, a plurality of first pixels 103, a plurality of second pixels 104, and a plurality of third pixels 105. A side irradiated with incident light is defined as a light-receiving surface.

The first substrate 101 and the second substrate 102 are stacked together. The first substrate 101 and the second substrate 102 are silicon substrates. The first substrate 101 transmits, part of the incident light.

The first pixels 103 are disposed on the first substrate 101. Each of the first pixels 103 includes a first photodiode 113 that detects light. The first pixel 103 is configured to output a first signal (a W signal or a white signal) corresponding to the exposure amount of incident light. Hereinafter, the first pixel 103 is also referred to as a W pixel.

The second pixels 104 are disposed on the first substrate 101. Each of the second pixels 104 includes a second photodiode 114 that detects blue light. The second pixel 104 is configured to output a second signal (a B signal or a blue signal) corresponding to the exposure amount of blue light from the incident light. Hereinafter, the second pixel 104 is also referred to as a B pixel.

The third pixels 105 are disposed on the second substrate 102. Each of the third pixels 105 includes a third photodiode 115 that detects red light. The third pixel 105 is configured to output a third signal (an R signal or a red signal) corresponding to the exposure amount of red light from the incident light transmitted through the first substrate 101. Hereinafter, the third pixel 105 is also referred to as an R pixel.

The depth of the first photodiode 113 is greater than the depth of the second photodiode. Therefore, the types of light detected by the first photodiode 113 and the second photodiode 114 are different. Although the depth of the first photodiode 113 is the same as the depth of the third photodiode 115, light detected by the first photodiode 113 and light detected by the third photodiode 115 are different since different light is incident thereon. In the shown example, the incident light is incident directly on the first photodiode 113. On the other hand, the incident light is incident on the third photodiode 115 after being transmitted through the first substrate 101.

Figure 2:
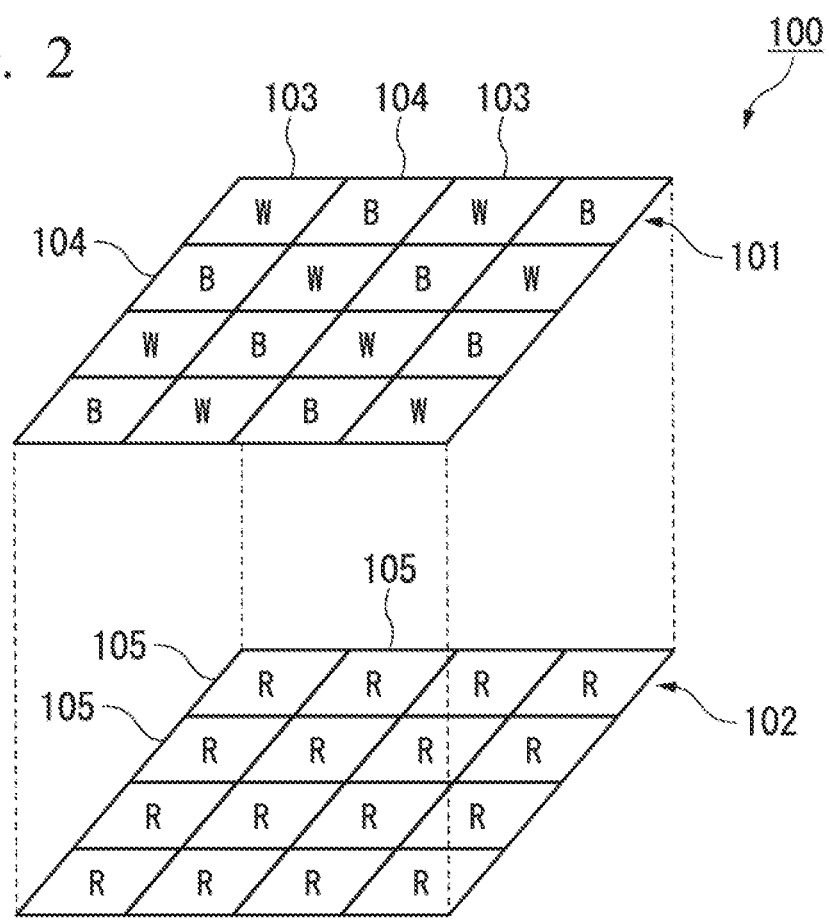
FIG. 2 is a schematic diagram showing the arrangement of first pixels, second pixels, and third pixels according to the first embodiment of the present invention.

Next, the arrangement of the first pixels 103, the second pixels 104, and the third pixels 105 will be described. FIG. 2 is a schematic diagram showing the arrangement of first pixels 103, second pixels 104, and third pixels 105 in the present embodiment. In the example shown in FIG. 2, the first substrate 101 includes eight first pixels 103 and eight second pixels 104 arranged regularly in a two-dimensional array of four rows and four columns. The second substrate 102 includes a total of sixteen third pixels 105 arranged regularly in a two-dimensional array of four rows and four columns.

As shown in FIG. 2, the first pixels 103 and the second pixels 104 are alternately arranged on the first substrate 101. The incident light is directly incident on the first pixels 103 and the second pixels 104. Therefore, the first substrate 101 can output first signals (W signals) corresponding to the exposure amount of the incident light and second signals (B signals) corresponding to the exposure amount of blue light from the incident light.

The third pixels 105 are disposed on the second substrate 102. Light transmitted through the first substrate 101 among the incident light is incident on the third pixels 105. The first substrate 101 is a silicon substrate and transmits light in a wavelength bandwidth including wavelengths of red light. Therefore, the second substrate 102 can output third signals (R signals) corresponding to the exposure amount of red light from the incident light.

Accordingly, with such an arrangement of the first pixels 103, the second pixels 104, and the third pixels 105, it is possible to simultaneously output first signals (W signals), second signals (B signals), third signals (R signals).

The numbers and arrangement of the first pixels 103 and the second pixels 104 included in the first substrate 101, and the numbers and arrangement of the third pixels 105 included in the second substrate 102, are not limited to those of the example shown in FIG. 2, and any respective numbers and arrangement thereof may be employed. In the example shown in FIG. 2, the third pixels 105 are disposed under the first pixels 103 and the second pixels 104 in correspondence therewith, but the present invention is not limited to such an arrangement. For example, it is possible to design a configuration such that the pixel size of the third pixel 105 is different from the pixel size of each of the first pixel 103 and the second pixel 104 (for example, such that the pixel size of the third pixel 105 is an integer multiple of that of the first pixel 103).

Figure 3:
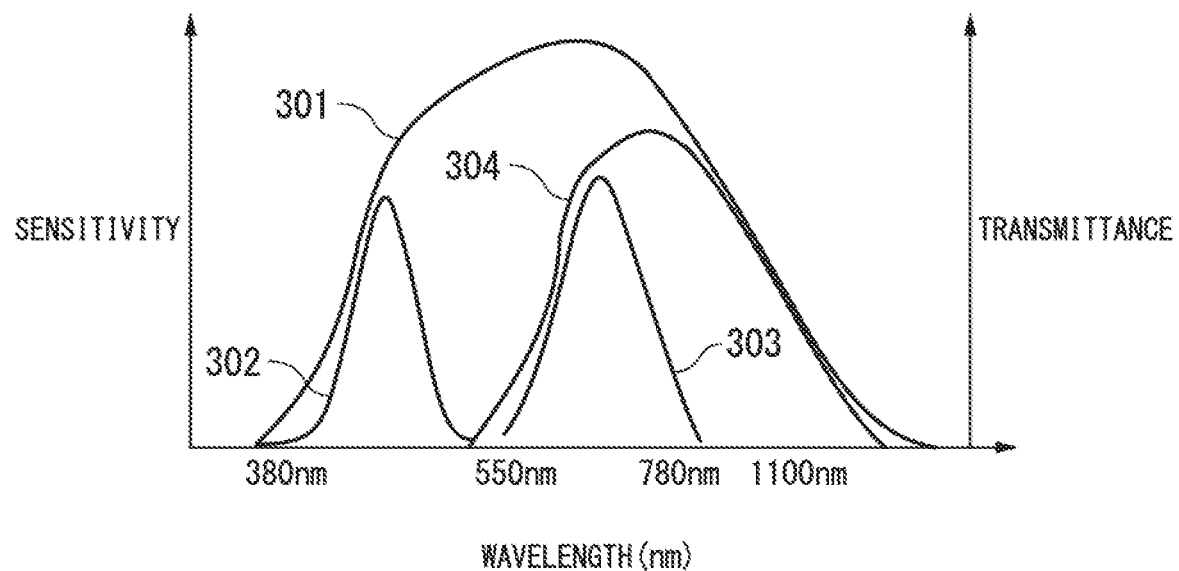
FIG. 3 is a graph showing the sensitivities of the first pixels, the second pixels, and the third pixels and the transmittance of a silicon substrate in the first embodiment of the present invention.

FIG. 3 is a graph showing the sensitivities of the first pixel 103, the second pixel 104, and the third pixel 105, and the transmittance of the silicon substrate in the present embodiment. The horizontal axis of the graph represents wavelength (nm). The left vertical axis of the graph shows the sensitivities of the first pixel 103, the second pixel 104, and the third pixel 105. The right vertical axis of the graph represents the transmittance of the silicon substrate.

A line 301 represents the sensitivity of the first pixel 103 (W pixel). As shown, the first pixel 103 has a sensitivity corresponding to a wavelength bandwidth of 380 nm to 1400 nm. The first pixel 103 has a sensitivity corresponding to a wavelength bandwidth including wavelengths of red light, wavelengths of green light, and wavelengths of blue light.

A line 302 represents the sensitivity of the second pixel 104 (B pixel). As shown, the second pixel 104 has a sensitivity corresponding to a wavelength bandwidth of 380 nm to 500 nm. The second pixel 104 has a sensitivity corresponding to a wavelength bandwidth including wavelengths of blue light.

A line 303 represents the sensitivity of the third pixel 105 (R pixel). As shown, the third pixel 105 has a sensitivity corresponding to a wavelength bandwidth of 550 nm to 800 nm. The third pixel 105 has a sensitivity corresponding to a wavelength bandwidth including wavelengths of red light.

A line 304 represents the transmittance of the silicon substrate. As shown, the silicon substrate transmits light in a wavelength bandwidth of 500 nm to 1500 nm. The silicon substrate transmits light in a wavelength bandwidth including wavelengths of red light. Accordingly, red light from the incident light is transmitted through the first substrate 101 and is incident on the second substrate 102. Therefore, even though the first substrate 101 and the second substrate 102 are stacked together, each of the third pixels 105 of the second substrate 102 can output a third signal (an R signal) corresponding to the exposure amount of red light from the incident light. Accordingly, pixels (for example, the third pixels 105) that detect light having long wavelengths can be used for the second substrate 102.

The silicon substrate does not transmit light in a wavelength bandwidth of blue light wavelength. Therefore, even if second pixels 104 are disposed on the second substrate 102, the second pixels 104 cannot output second signals corresponding to the exposure amount of blue light from the incident light. Accordingly, pixels (for example, the second pixels 104) that detect light having short wavelengths cannot be used for the second substrate 102.

Figure 4:
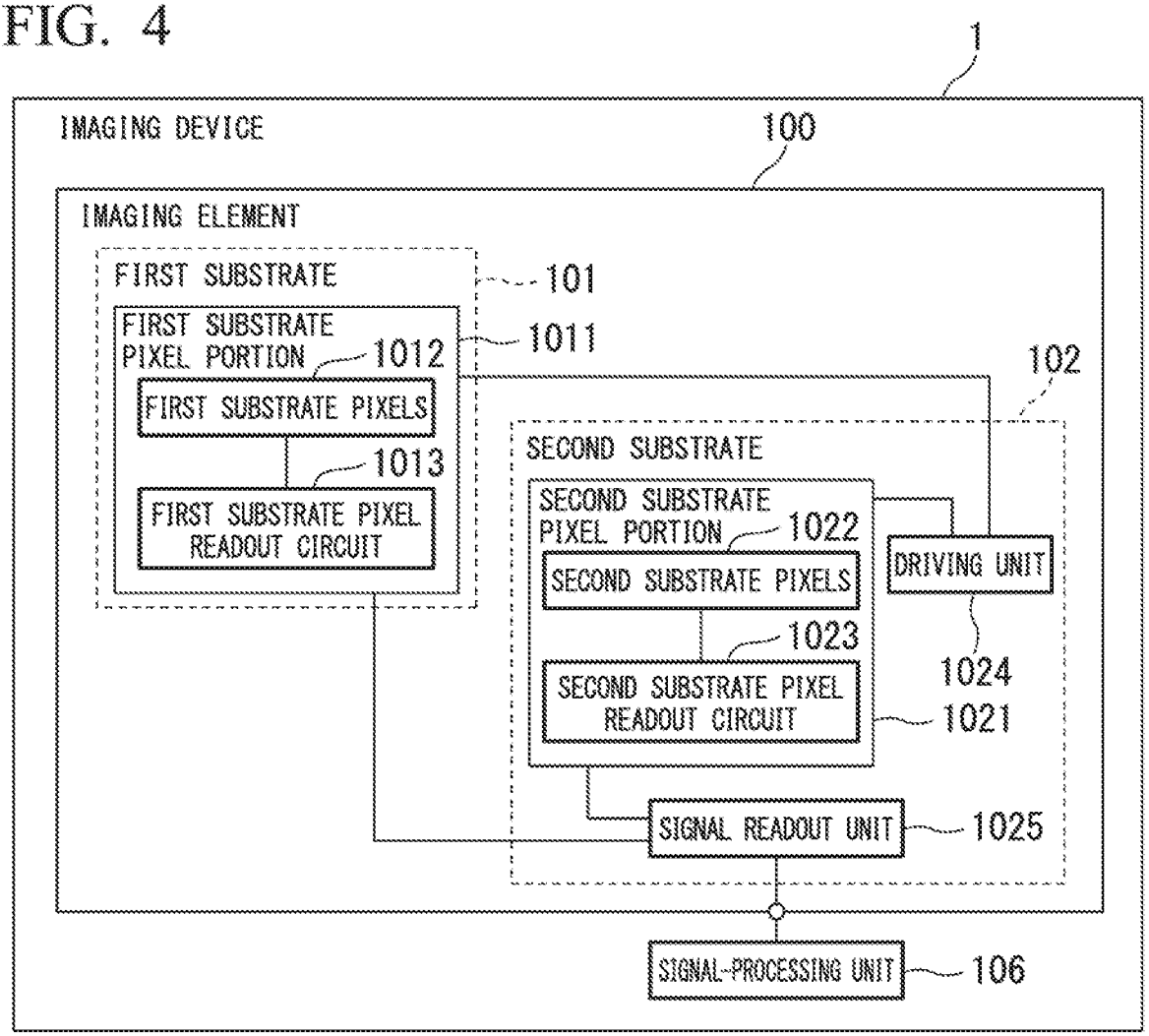
FIG. 4 is a block diagram showing a configuration of an imaging device according to the first embodiment of the present invention.

Next, the configuration of the imaging device 1 will be described. FIG. 4 is a block diagram showing the configuration of the imaging device 1 according to the present embodiment. The imaging device 1 includes the imaging element 100 and a signal-processing unit 106. The imaging element 100 includes the first substrate 101 and the second substrate 102. The first substrate 101 includes a first substrate pixel portion 1011.

The first substrate pixel portion 1011 includes first substrate pixels 1012 and a first substrate pixel readout circuit 1013. The first substrate pixels 1012 include the plurality of first pixels 103 and the plurality of second pixels 104 described above. The second substrate 102 includes a second substrate pixel portion 1021, a driving unit 1024, and a signal readout unit 1025. The second substrate pixel portion 1021 includes second substrate pixels 1022 and a second substrate pixel readout circuit 1023. The second substrate pixels 1022 include the plurality of third pixels 105 described above.

The driving unit 1024 transmits control signals to drive the first substrate pixel portion 1011 and the second substrate pixel portion 1021. The signal readout unit 1025 includes a circuit for removing signal noise, a circuit for performing A/D conversion, and a scanning circuit. The signal readout unit 1025 controls the first substrate pixel readout circuit 1013 to read first signals and second signals from the first substrate pixels 1012. The signal readout unit 1025 also controls the second substrate pixel readout circuit 1023 to read third signals from the second substrate pixels 1022.

The signal-processing unit 106 generates an image using the first signals, the second signals, and the third signals read by the signal readout unit 1025. Specifically, the signal-processing unit 106 performs calculation using first signals (W signals), second signals (B signals), and third signals (R signals) to generate green light signals (G signals). The signal-processing-unit 106 generates an RGB image using the second signals (B signals), the third signals (R signals), and the generated green light signals (G signals). The signal-processing unit 106 generates an NBI image using the second signals (B signals).

Signal transmission between the first substrate 101 and the second substrate 102 may be performed in any manner. For example, through-electrodes may be provided between the first substrate 101 and the second substrate 102 to transmit signals between the first substrate 101 and the second substrate 102. For example, transmission paths may also be provided outside the first substrate 101 and the second substrate 102 to transmit signals between the first substrate 101 and the second substrate 102.

Figure 5:
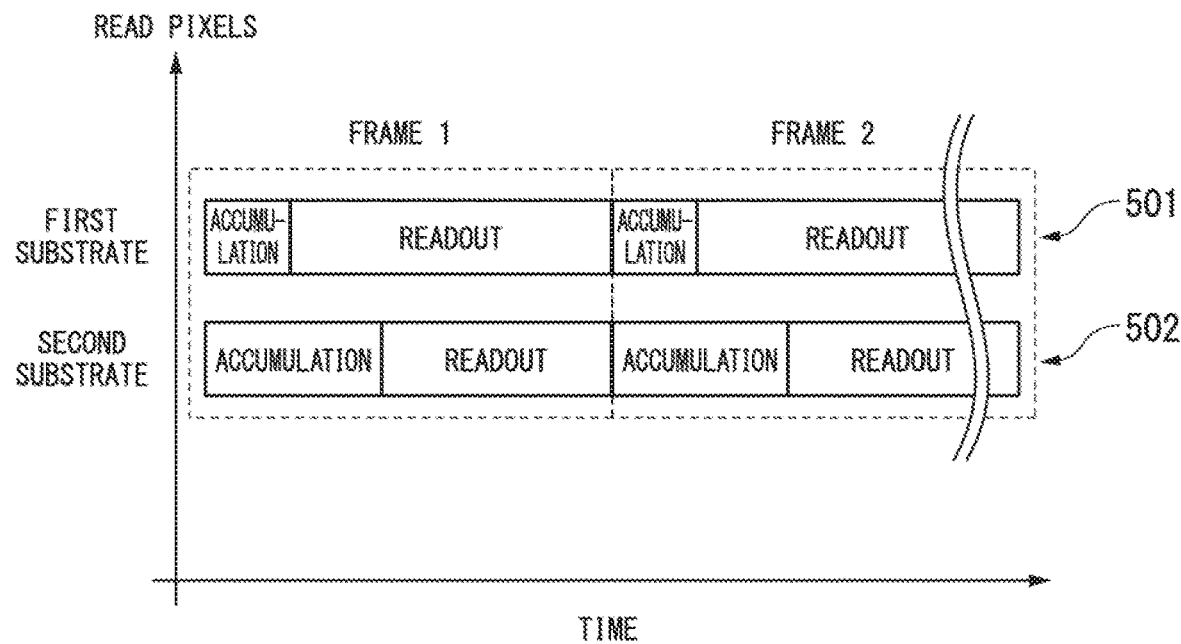
FIG. 5 is a timing chart diagram showing the drive timings of the imaging element according to the first embodiment of the present invention.

Next, the drive timings of the imaging element 100 will be described. FIG. 5 is a timing chart diagram showing the drive timings of the imaging element 100 according to the present embodiment. The shown example illustrates a timing chart 501 showing the drive timings of the first pixels 103 and the second pixels 104 included in the first substrate 101, and a timing chart 502 showing the drive timings of the third pixels 105 included in the second substrate 102. The horizontal axis of the timing charts represents time.

As shown, in the present embodiment, the charge accumulation time (exposure time) of each of the third pixels 105 is longer than the charge accumulation time (exposure time) of each of the first pixels 103 and the second pixels 104. Since only light which has been transmitted through the first substrate 101 is emitted to the third pixel 105, the third pixel 105 is irradiated with a smaller amount of light than the amount of light emitted to the first pixel 103 and the second pixel 104. In the present embodiment, the readout time of each pixel during which a signal is read from the pixel is set such that the exposure start timing of each of the first pixels 103, the second pixels 104, and the third pixels 105 is the same as the start timing of the same frame.

According to the present embodiment, the first substrate 101 and the second substrate 102 are stacked together as described above. The second substrate 102 is disposed at the side opposite to the light-receiving surface of the first substrate 101 at a position which overlaps with the first substrate 101 as seen from the light-receiving surface of the first substrate 101. The first substrate 101 transmits light. The light transmitted through the first substrate 101 is emitted to the second substrate 102.

The first pixels 103 and the second pixels 104 of the first substrate 101, and the third pixels 105 of the second substrate 102 can be exposed at the same time. That is, generation of first signals by the first pixels 103, generation, of second signals, by the second pixels 104, and generation of third signals by the third pixels 105 can be performed at the same time. Accordingly, the signal-processing unit 106 can simultaneously generate an RGB image based on the first signals (W signals), the second signals (B signals), and the third signals (R signals) and an NBI image obtained by performing emphasis processing based on the second signals (B signals).

As described above, in the present embodiment, the proportion of the second pixels 104 is two pixels in every four in the pixels included in the first substrate 101. Accordingly, it is possible to acquire more second signals (B signals) and therefore it is possible to improve the resolution of the NBI image. In the present embodiment, a green light signal (a G signal) is generated using a first signal (a W signal), a second signal (a B signal), and a third signal (an R signal). The proportion of the first pixels 103 is two pixels in every four in the pixels included in the first substrate 101. The proportion of the second pixels 104 is two pixels in every four in the pixels included in the first substrate 101. Further, the proportion of the third pixels 105 is all pixels of the second substrate 102, Accordingly, it is possible to improve the resolution of the green light signal (G signal) and thus to improve the resolution, of the RGB image.

In the above example, the first pixel 103, the second pixel 104, and the third pixel 105 generate different types of signals by making the thicknesses or incident light of the photodiodes 113 to 115 different from each other, but the present invention is not limited to this. For example, it is possible to allow the first pixel, the second pixel, and the third pixel to generate different types of signals by providing different color filters for the first, second, and third pixels.

Figure 6:
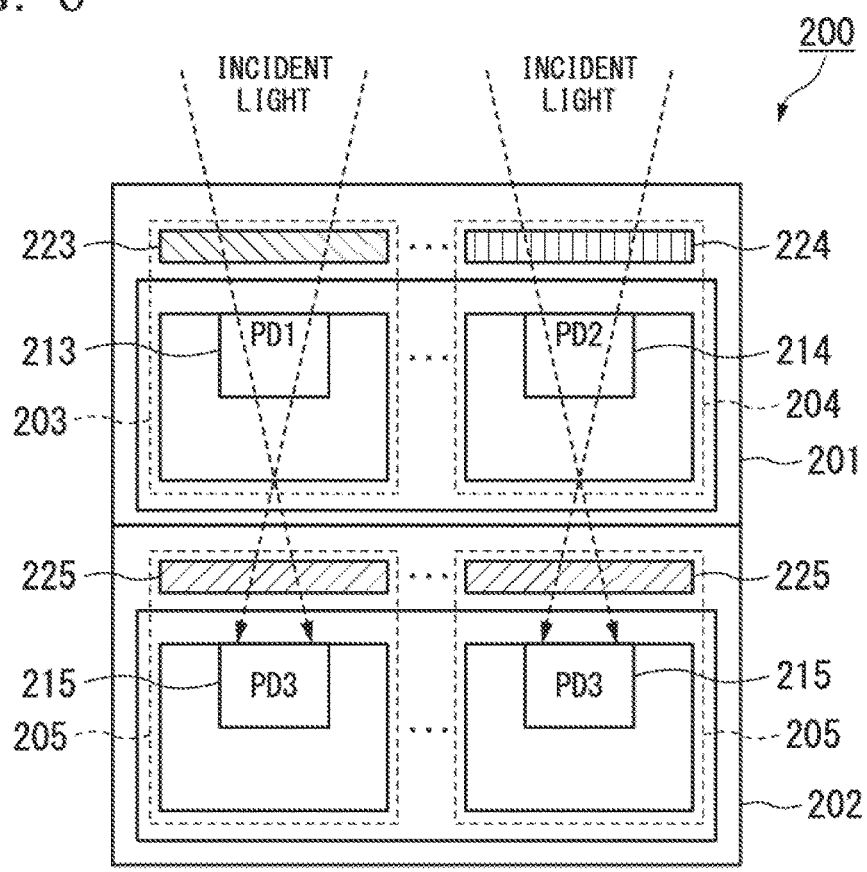
FIG. 6 is a cross-sectional view showing a cross section of an imaging element in which a first pixel, a second pixel, and a third pixel include different color filters in the first embodiment of the present invention.

FIG. 6 is a cross-sectional view showing a cross section of an imaging element 200 having the first pixels 203, the second pixels 204, and the third pixels 205, wherein the first pixels 203, the second pixels 204, and the third pixels 205 including different color filters according to the present embodiment. In the shown example, the imaging element 200 includes a first substrate 201, a second substrate 102, a plurality of first pixels 203, a plurality of second pixels 204, and a plurality of third pixels 205. A side irradiated with incident light is defined as a light-receiving surface.

The first substrate 201 and the second substrate 202 are stacked together. The first substrate 201 and the second, substrate 202 are silicon substrates. The first substrate 201 transmits part of the incident light.

The first pixels 203 are disposed on the first substrate 201. Each of the first pixels 203 includes a first photodiode 213 that detects light and a color filter 223 that transmits light of all wavelengths. The first pixel 203 is configured to output a first signal (a W signal or a white signal) corresponding to the exposure amount of incident light. A color filter that does not transmit only infrared light may be used as the color filter 223.

The second pixels 204 are disposed on the first substrate 201. Each of the second pixels 204 includes a second photodiode 214 that detects light and a color filter 224 that transmits only blue light. The second pixel 204 is configured to output a second signal (a B signal or a blue signal) corresponding to the exposure amount of blue light from the incident light.

The third pixels 205 are disposed on the second substrate 202. Each of the third pixels 205 includes a third photodiode 215 that detects light and a color filter 225 that transmits only red light. The third pixel 205 is configured to output a third signal (an R signal or a red signal) corresponding to the exposure amount of red light from the incident light transmitted through the first substrate 201.

The arrangement, of the first pixels 203, the second pixels 204, and the third pixels 205 is similar to the arrangement of the first pixels 103, the second pixels 104, and the third pixels 105 shown in FIG. 2. Further, the configuration and operation of the imaging device including the imaging element 200 are similar to the configuration and operation of the imaging device 1 illustrated in FIG. 4.

Therefore, the imaging device including the imaging element 200 can simultaneously generate an RGB image and an NBI image obtained by performing emphasis processing based on second signals (B signals), similar to the above-described imaging device 1. The imaging device including the imaging element 200 can improve the resolution of the NBI image, similar to the imaging device 1 described above. The imaging device including the imaging element 200 can improve the resolution of the RGB image, similar to the imaging device 1 described above.

Second Embodiment

Next, a second embodiment of the present invention will be described. The difference between the imaging device according to the present second embodiment and the imaging device 1 according to the first embodiment is the configuration of the imaging element. The difference between the imaging element 100 according to the first embodiment and an imaging element 400 according to the present embodiment is that circuit portions 406 are provided on a second substrate 402. Other configurations and operations of the imaging device according to the present embodiment are similar to those of the imaging device according to the first embodiment.

Figure 7:
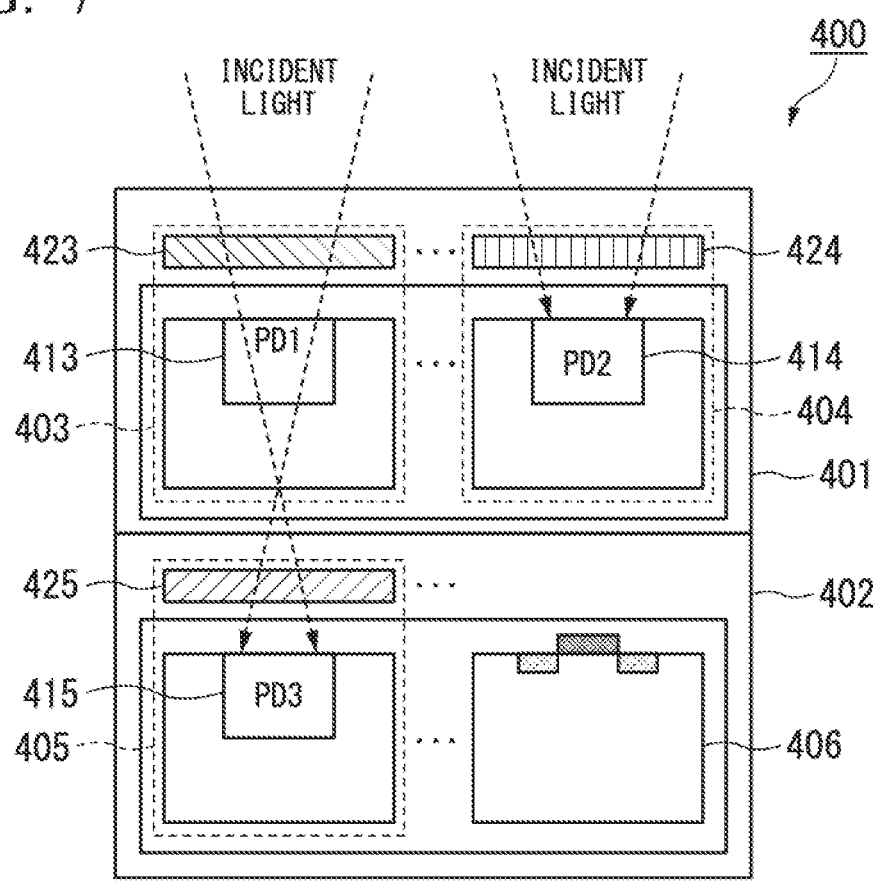
FIG. 7 is a cross-sectional view showing a cross section of an imaging element according to a second embodiment of the present invention.

FIG. 7 is a cross-sectional view showing a cross section of the imaging element 400 according to the second embodiment of the present invention. In the shown example, the imaging element 400 includes a first substrate 401, a second substrate 402, a plurality of first pixels 403, a plurality of second pixels 404, a plurality of third pixels 405, and circuit portions 406. A side irradiated with incident light is defined as a light-receiving surface.

The first pixels 403 are disposed on the first substrate 401. Each of the first pixels 403 includes a first photodiode 413 that detects light and a color filter 423 that transmits light of all wavelengths. The first pixel 403 is configured to output a first signal (a W signal or a white signal) corresponding to the exposure amount of incident light. A color filter that does not transmit only infrared light may be used as the color filter 423.

The second pixels 404 are disposed on the first substrate 401. Each of the second pixels 404 includes a second photodiode 414 that detects light and a color filter 424 that transmits only blue light. The second pixel 404 is configured to output a second signal (a B signal or a blue signal) corresponding to the exposure amount of blue light from the incident light.

The third pixels 405 are disposed on the second substrate 402. Each of the third pixels 405 includes a third photodiode 415 that detects light and a color filter 425 that transmits only red light. The third pixel 405 is configured to output a third signal (an R signal or a red signal) corresponding to the exposure amount of red light from the incident light transmitted through the first substrate 401.

The circuit portions 406 include circuits such as a driving unit 1024 and a signal readout unit 1025. Thus, circuits such as the driving unit 1024 and the signal readout unit 1025 can be arranged in the circuit portions 406.

Figure 8:
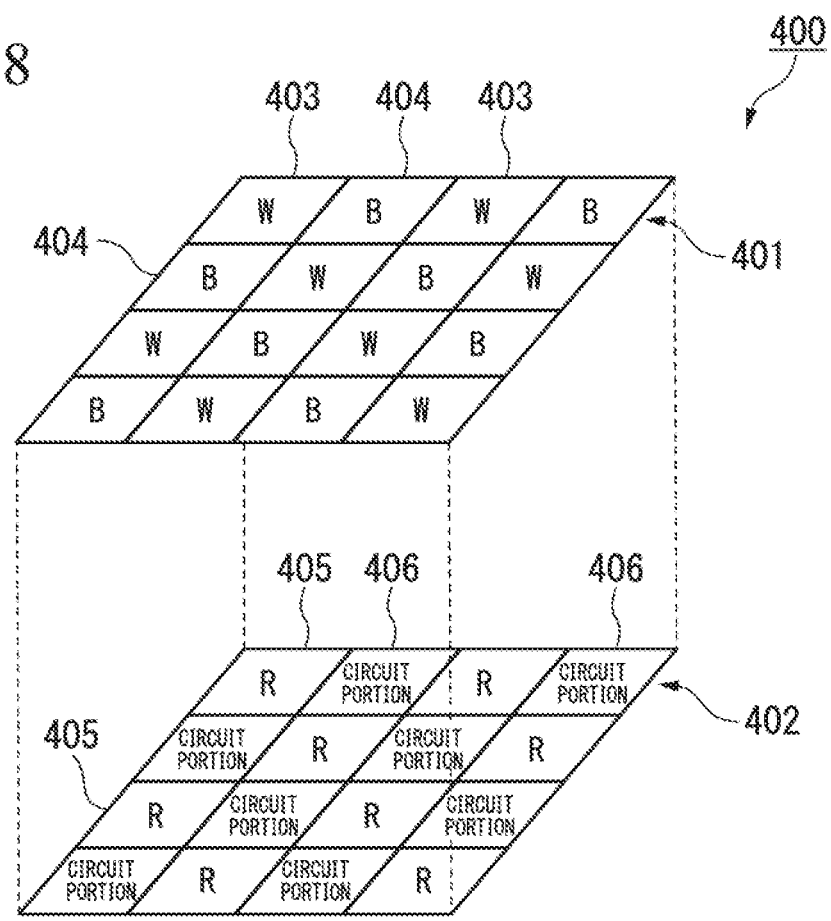
FIG. 8 is a schematic diagram showing the arrangement of first pixels, second pixels, third pixels, and circuit portions according to the second embodiment of the present invention.

Next, the arrangement of the first pixels 403, the second pixels 404, the third pixels 405, and the circuit portions 406 will be described. FIG. 8 is a schematic diagram showing the arrangement of first pixels 403, second pixels 404, third pixels 405, and circuit portions 406 in the present embodiment. In the example shown in FIG. 8, the first, substrate 401 includes eight first pixels 403 and eight second pixels 404 arranged regularly in a two-dimensional array of four rows and four columns. The second substrate 402 includes eight third pixels 405 and eight circuit portions 406 arranged regularly in a two-dimensional array of four rows and four columns.

As shown in FIG. 8, the first pixels 403 and the second pixels 404 are alternately arranged on the first substrate 401. The incident light is incident directly on the first pixels 403 and the second pixels 404. Therefore, the first substrate 401 can output first signals (W signals) corresponding to the exposure amount of the incident light and second signals (B signals) corresponding to the exposure amount of blue light from the incident light.

The third pixels 405 and the circuit portions 406 are alternately arranged on the second substrate 402. The third pixels 405 are disposed at positions where light transmitted through the first pixels 403 is incident. That is, the third pixels 405 are disposed under the first pixels 403. Further, the circuit portions 406 are disposed under the second pixels 404.

According to the arrangement, light transmitted through the first pixels 403 of the first substrate 101 among the incident light is incident on the third pixels 405. The color filter 423 included in each of the first pixels 403 transmits all light. The first substrate 401 is a silicon substrate and transmits light in a wavelength bandwidth including wavelengths of red light. Therefore, each of the third pixels 405 of the second substrate 402 can output a third signal (an R signal) corresponding to the exposure amount of red light from the incident light.

The color filter 424 included in each of the second pixels 404 transmits only blue light. That is, the color filter 424 does not transmit red light. Thus, the light transmitted through the second pixels 404 does not include red light. Therefore, even if the third pixels 405 are disposed under the second pixels 404, it is difficult to accurately detect red light. For example, when circuits such as the driving unit 1024, the signal readout unit 1025, the second substrate pixel readout circuit 1023, or the like are arranged around the third pixels 405, it is conceivable that the aperture ratio of the third pixels 405 will decrease and the S/N ratio of third signals will decrease.

In the present embodiment, it is possible to increase the aperture ratio of the third pixels 405 by arranging the driving unit 1024, the signal readout unit 1025, the second substrate pixel readout circuit 1023, or the like as the circuit portions 406 under the second pixels 404 which do not transmit red light. Therefore, it is possible to increase the S/N ratio of third signals output by the third pixels 405.

The respective numbers and arrangement of the first pixels 403 and the second pixels 404 included in the first substrate 401 and the third pixels 405 and the circuit portions 406 included in the second substrate 402 are not limited to those of the example shown in FIG. 8, and any respective numbers and arrangement thereof may be employed. In the example shown in FIG. 8, the third pixels 405 are disposed under the first pixels 403 in correspondence therewith, but the present invention is not limited to this. For example, it is possible to design a configuration such that the pixel size of the third pixel 405 is different from the pixel size of the first pixel 403 (for example, such that the pixel size of the third pixel 405 is an integer multiple of that of the first pixel 403). For example, it is possible to design a configuration such that the size of the circuit portion 406 is different from the pixel size of the second pixel 404.

The configuration and operation, of the imaging device including the imaging element 400 are similar to those of the imaging device 1 according to the first embodiment. For example, the method or generating an NBI image and the method of generating an RGB image by the signal-processing unit 106 are similar to those of the first embodiment.

Third Embodiment

Next, a third embodiment of the present invention will be described. The difference between the imaging device according to the present embodiment and the imaging device according to the second embodiment is the configuration of the imaging element. The difference between the imaging element 400 in the second embodiment and an imaging element 600 in the present embodiment is the number and arrangement of circuit portions 606 provided on a second substrate 602. Other configurations of the imaging device according to the present embodiment are similar to those of the imaging device according to the second embodiment.

Figure 9:
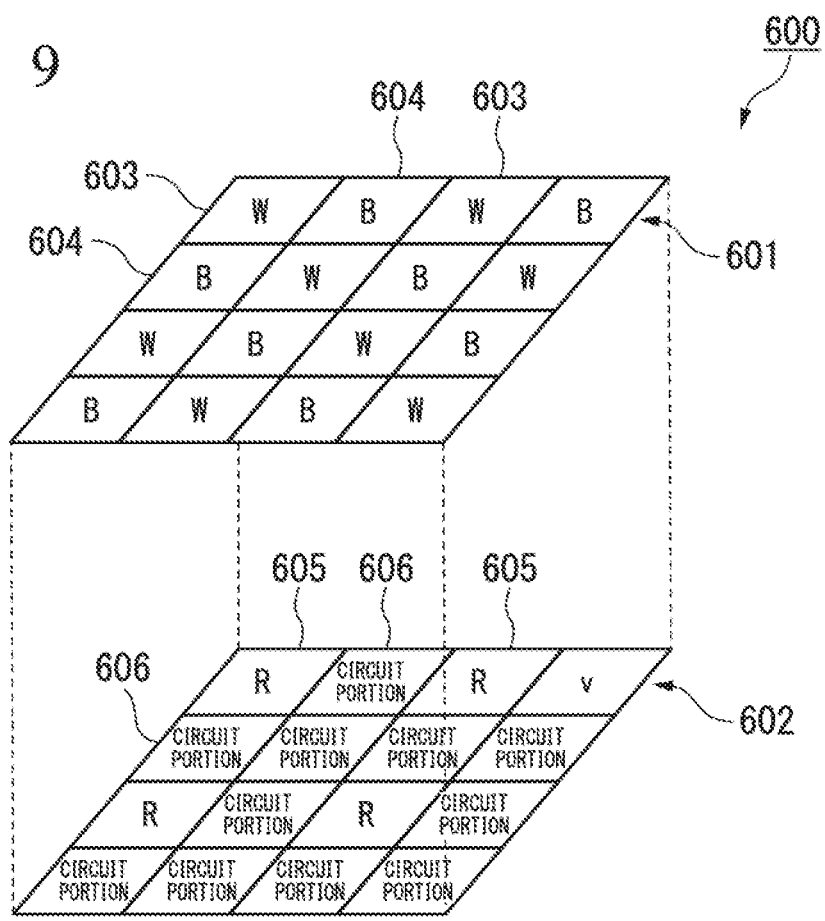
FIG. 9 is a schematic diagram showing the arrangement of first pixels, second pixels, third pixels, and circuit portions according to a third embodiment of the present invention.

FIG. 9 is a schematic diagram showing the arrangement of first pixels 603, second pixels 604, third pixels 605, and circuit portions 606 in the present embodiment. In the example shown in FIG. 9, a first substrate 601 includes eight first pixels 603 and eight second pixels 604 arranged regularly in a two-dimensional array of four rows and four columns. The second substrate 602 includes four third pixels 605 and twelve circuit portions 606 arranged regularly in a two-dimensional array of four rows and four columns.

As shown in FIG. 9, the first pixels 603 and the second pixels 604 are alternately arranged on the first substrate 601. The incident light is incident directly on the first pixels 603 and the second pixels 604. Therefore, the first substrate 601 can output first signals (W signals) corresponding to the exposure amount of the incident light and second signals (B signals) corresponding to the exposure amount of blue light from the incident light.

Third pixels 605 and circuit portions 606 are alternately arranged in odd-numbered rows of the second substrate 602. Circuit portions 606 are arranged in even-numbered rows of the second substrate 602. The third pixels 605 are disposed at positions where light transmitted through the first pixels 603 is incident. That is, the third pixels 605 are disposed under the first pixels 603.

According to the arrangement, light transmitted through the first pixels 603 of the first substrate 601 among the incident light is incident, on the third pixels 605. A color filter (which is the same as the color filter 423 of the embodiment) included in each of the first pixels 603 transmits all light. The first substrate 601 is a silicon substrate and transmits light in a wavelength bandwidth including wavelengths of red light. Therefore, each of the third pixels 605 of the second substrate 602 can output a third signal (an R signal) corresponding to the exposure amount of red light from the incident light.

As described above, in the present embodiment, by increasing the number of the circuit portions 606 as compared with the second embodiment, for example, a first substrate pixel readout circuit 1013 disposed on the first substrate 601 can be arranged on the circuit portions 606. Thus, it is not necessary to dispose the first substrate pixel readout circuit 1013 on the first substrate 601 and it is thus possible to increase the aperture ratios of the first pixels 603 and the second pixels 604. Therefore, it is possible to increase the S/N ratios of first signals output by the first pixels 603 and second signals output by the second pixels 604.

The respective numbers and arrangement of the first pixels 603 and the second pixels 604 included in the first substrate 601 and the third pixels 605 and the circuit portions 606 included in the second substrate 602 are not limited to those of the example shown in FIG. 9, and any respective numbers and arrangement thereof may be employed. In the example shown, in FIG. 9, the third pixels 605 are disposed under the first pixels 603 in correspondence therewith, but the present invention is not limited to this. For example, it is possible to design a configuration such that the pixel size of the third pixel 605 is different from the pixel size of the first pixel 603 (for example, such that the pixel size of the third pixel 605 is an integer multiple of that of the first pixel 603). Further, for example, it is possible to design a configuration such that the size of the circuit portion 606 is different from the pixel size of the first pixel 603 or the second pixel 604.

The configuration and operation of the imaging device including the imaging element 600 are similar to those of the imaging device according to the second embodiment. For example, the method of generating an NBI image and the method of generating an RGB image by the signal-processing unit 106 are similar to those of the second embodiment.

Fourth Embodiment

Next, a fourth embodiment of the present invention will be described. The difference between the imaging device according to the present embodiment and the imaging device 1 according to the first embodiment is the configuration of the imaging element. The difference between the imaging element 100 in the first embodiment and an imaging element 700 in the present embodiment is that bonding electrodes 706 are provided between a first substrate 701 and a second substrate 702 and no third pixels 705 are provided at positions on the second substrate 702 where the bonding electrodes 706 are provided. Other configurations and operations of the imaging element 700 according to the present embodiment are similar to those of the imaging element 100 according to the first embodiment.

Figure 10:
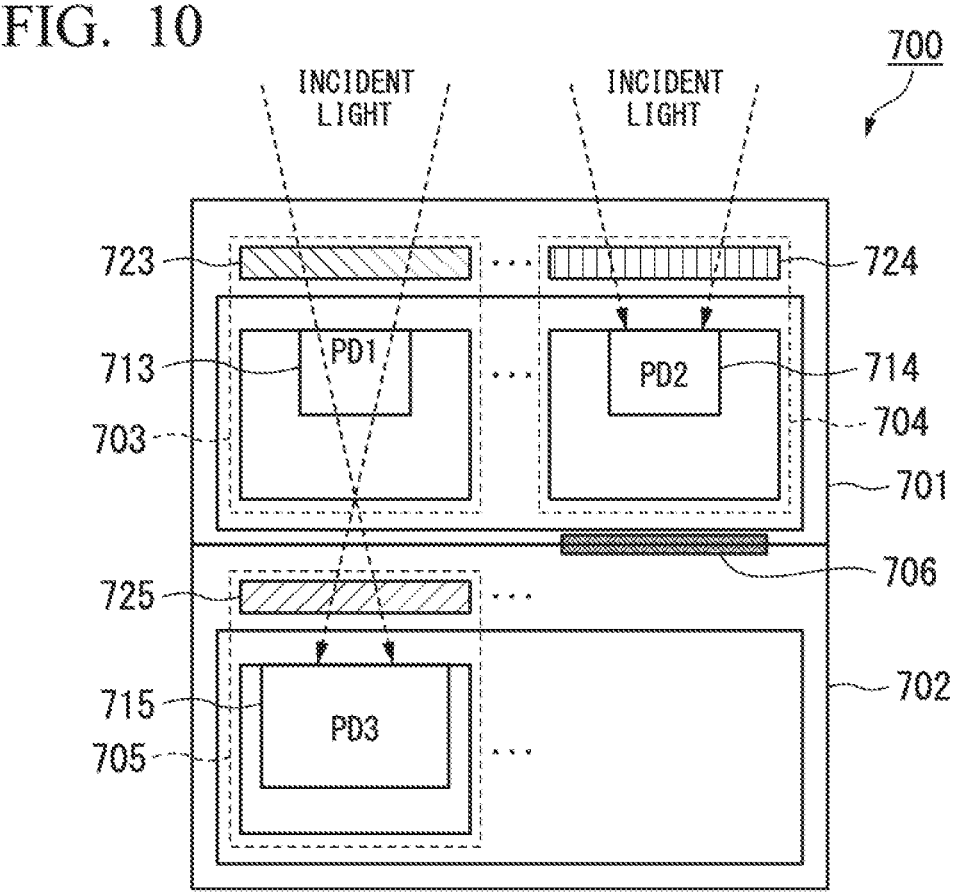
FIG. 10 is a cross-sectional view showing a cross section of an imaging element according to a fourth embodiment of the present invention.

FIG. 10 is a cross-sectional view showing a cross section of the imaging element 700 according to the fourth embodiment of the present invention. In the shown example, the imaging element 700 includes the first substrate 701, the second substrate 702, a plurality of first pixels 703, a plurality of second pixels 704, a plurality of third pixels 705, and the bonding electrodes 706. A side irradiated with incident light is defined as a light-receiving surface.

The first pixels 703 are disposed on the first substrate 701. Each of the first pixels 703 includes a first photodiode 713 that detects light and a color filter 723 that transmits light of all wavelengths. The first pixel 703 is configured to output a first signal (a W signal or a white signal) corresponding to the exposure amount of incident light. A color filter that does not transmit only infrared light may be used as the color filter 423.

The second pixels 704 are disposed on the first substrate 701. Each of the second pixels 704 includes a second photodiode 714 that detects light and a color filter 724 that transmits only blue light. The second pixel 704 is configured to output a second signal (a B signal or a blue signal) corresponding to the exposure amount of blue light from the incident light.

The third pixels 705 are disposed on the second substrate 702. Each of the third pixels 705 includes a third photodiode 715 that detects light and a color filter 725 that transmits only red light. The third pixel 705 to output, a third signal (an R signal or a red signal) corresponding to the exposure amount of red light from the incident light transmitted through the first substrate 701.

The bonding electrodes 706 transmit signals between the first substrate 701 and the second substrate 702. According to the configuration, signals can be transmitted between the first substrate 701 and the second substrate 702.

Figure 11:
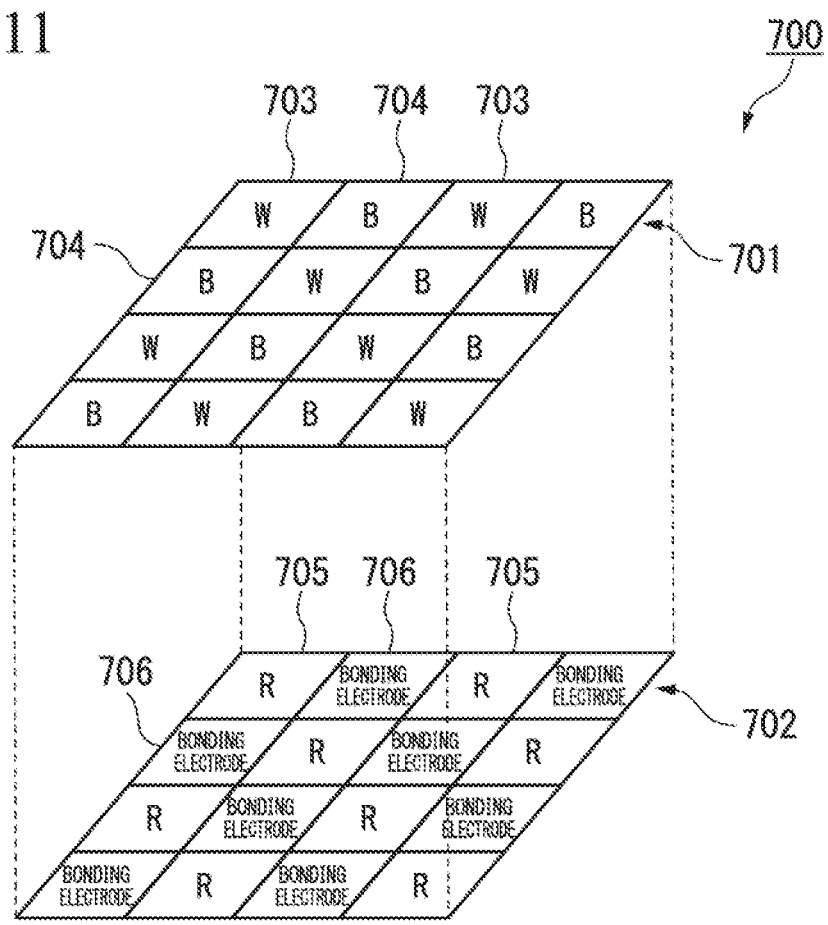
FIG. 11 is a schematic diagram showing the arrangement of first pixels, second pixels, third pixels, and bonding electrodes according to the fourth embodiment of the present invention.

Next, the arrangement of first pixels 703, second pixels 704, third pixels 705, and bonding electrodes 706 will be described. FIG. 11 is a schematic diagram showing the arrangement of first pixels 703, second pixels 704, third pixels 705, and bonding electrodes 706 in the present embodiment. In the example shown in FIG. 11, the first substrate 701 includes eight first pixels 703 and eight second pixels 704 arranged regularly in a two-dimensional array of four rows and four columns. The second substrate 702 includes eight third pixels 705 and eight bonding electrodes 706 arranged regularly in a two-dimensional pattern of four rows and four columns.

As shown in FIG. 11, the first pixels 703 and the second pixels 704 are alternately arranged on the first substrate 701. The incident light is directly incident on the first pixels 703 and the second pixels 704. Therefore, the first substrate 701 can output first signals (W signals) corresponding to the exposure amount of the incident light and second signals (B signals) corresponding to the exposure amount of blue light from the incident light.

The third pixels 705 and the bonding electrodes 706 are alternately arranged on the second substrate 702. The third pixels 705 are disposed at positions where light transmitted through the first pixels 703 is incident. That is, the third pixels 705 are disposed under the first pixels 703. The bonding electrodes 706 are disposed under the second pixels 704.

According to the arrangement, light transmitted through the first pixels 703 of the first substrate 701 among the incident light is incident on the third pixels 705. The color filter 723 included in each of the first pixels 703 transmits all light. The first substrate 701 is a silicon substrate and transmits light in a wavelength bandwidth including wavelengths of red light. Therefore, each of the third pixels 705 of the second substrate 702 can output a third signal (an R signal) corresponding to the exposure amount of red light from the incident light.

The color filter 724 included in each of the second pixels 704 transmits only blue light. That is, the color filter 724 does not transmit red light. Thus, light transmitted through the second pixel 704 does not include red light. Therefore, even if the third pixels 705 are disposed under the second pixels 704, it is difficult to accurately detect red light. For example, when bonding electrodes or the like are provided between the first substrate 701 and the second substrate 702 to transmit signals between the first substrate 701 and the second substrate 702, it is conceivable that the aperture ratio of the third pixels 705 will decrease. Further, when the aperture ratio of the third pixel 705 decreases, it is conceivable that the S/N ratio of third signals output by the third pixel 705 will decrease.

In the present embodiment, it is possible to increase the aperture ratio of the third pixels 705 by disposing the bonding electrodes 706 under the second pixels 704 which do not transmit red light. Therefore, it is possible to increase the S/N ratio of third signals output by the third pixels 705.

The respective numbers and arrangement of the first pixels 703 and the second pixels 704 included in the first substrate 701 and the third pixels 705 and the bonding electrodes 706 included in the second substrate 702 are not limited to those of the example shown in FIG. 11, and any respective numbers and arrangement thereof may be employed. In the example shown in FIG. 11, the third pixels 705 are disposed under the first pixels 703 in correspondence therewith, but the present invention is not limited to this. For example, it is possible to design a configuration such that the pixel size of the third pixel 705 is different from the pixel size of the first pixel 703 (for example, such that the pixel size of the third pixel 705 is an integer multiple of that of the first pixel 703). Further, for example, it is possible to design a configuration such that the size of the bonding electrode 706 is different from the pixel size of the second pixel 704.

The configuration and operation of the imaging device including the imaging element 700 are similar to those of the imaging device 1 according to the first embodiment. For example, the method of generating an NBI image and the method of generating an RGB image by the signal-processing unit 106 are similar to those of the first embodiment.

Fifth Embodiment

Next, a fifth embodiment of the present invention will be described. The difference between the imaging device according to the present embodiment and the imaging device 1 according to the first embodiment is the configuration of the imaging element. The difference between the imaging element 100 according to the first embodiment and an imaging element 800 in the present embodiment is that fourth pixels 806, which output fourth signals (G signals, green signals) corresponding to the exposure amount of green light from the incident light, are provided on a first substrate 801. Other configurations are similar to those of the first embodiment.

Each of the fourth pixels 806 may include a photodiode that detects green light to output a fourth signal corresponding to the exposure amount of green light from the incident light. Each of the fourth pixels 806 may also include a photodiode that detects light and a color filter that transmits only green light to output a fourth signal corresponding to the exposure amount of green light from the incident light.

Figure 12:
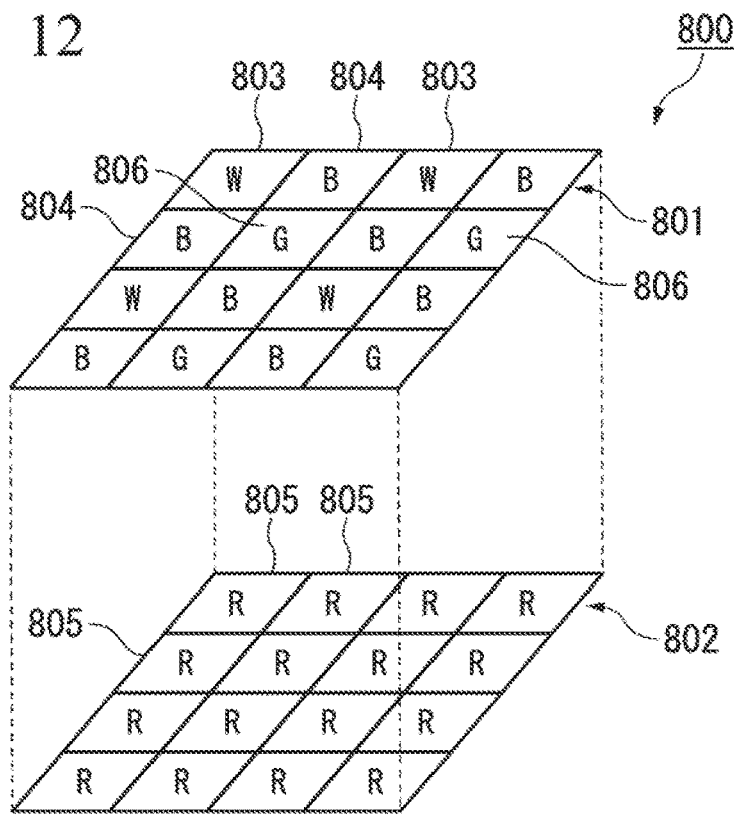
FIG. 12 is a schematic diagram showing the arrangement of first pixels, second pixels, third pixels, and fourth pixels according to a fifth embodiment of the present invention.

FIG. 12 is a schematic diagram showing an arrangement of first pixels 803, second pixels 804, third pixels 805, and fourth pixels 806 in the present embodiment. In the example shown in FIG. 12, the first substrate 801 includes four first pixels 803, eight second pixels 804 and four third pixels 806 arranged regularly in a two-dimensional array of four rows and four columns. The second substrate 802 includes sixteen third pixels 405 arranged regularly in a two-dimensional array of four rows and four columns.

As shown in FIG. 12, first pixels 803 and second pixels 804 are alternately arranged in odd-numbered rows of the first substrate 801. Second pixels 804 and fourth pixels 806 are alternately arranged in even-numbered rows of the first substrate 801. The incident light is directly incident on the first pixels 803, the second pixels 804, and the fourth pixels 806. Therefore, the first substrate 801 can output first signals (W signals) corresponding to the exposure amount of the incident light, second signals (B signals) corresponding to the exposure amount of blue light from the incident light, and fourth signals (G signals) corresponding to the exposure amount of green light from the incident light.

The third pixels 805 are disposed on the second substrate 802. Light transmitted through the first substrate 801 among the incident light is incident an the third pixels 805. The first substrate 801 is a silicon substrate and transmits light in a wavelength bandwidth including wavelengths of red light. Thus, the second substrate 802 can output third signals (R signals) corresponding to the exposure amount of red light from the incident light.

Accordingly, with such an arrangement of the first pixels 803, these con d pixels 804, the third pixels 805, and the fourth pixels 806, it is possible to simultaneously output first signals (W signals), second signals (B signals), third signals (R signals), and fourth signals (G signals).

The respective numbers and arrangement of the first pixels 803, the second pixels 804, and the fourth pixels 806 included in the first substrate 801, and the third pixels 805 included in the second substrate 802 are not limited to those of the example shown in FIG. 12, and any respective numbers and arrangement thereof may be employed. In the example shown in FIG. 12, the third pixels 805 are disposed under the first pixels 803, the second pixels 804, and the fourth pixels 806 in correspondence therewith, but the present invention is not limited to this. For example, it is possible to design a configuration such that the pixel size of the third pixel 805 is different from the pixel size of each of the first pixel 803, the second pixel 804, and the fourth pixel 806 (for example, such that the pixel, size of the third pixel 805 is an integer multiple or that of the first pixel 803).

Next, a method of generating an RGB image and an NBI image in the present embodiment will be described. The signal-processing unit 106 generates an image using a second signal, a third signal, and a fourth signal read by the signal readout unit 1025. More specifically, the signal-processing unit 106 generates an RGB image using a second signal (a B signal), a third signal (an R signal), and a fourth signal (a G signal). In addition, the signal-processing unit 106 generates an NBI image using the second signal (B signal).

A green light signal (G signal) may be generated by performing calculation using a first signal (W signal), a second signal (B signal), and a third signal (R signal). Both of the generated green light signal (G signal) and the fourth signal (G signal) may then be used to generate an RGB image.

According to the present embodiment, by providing the fourth pixels 806 on the first substrate 801, it is possible to obtain G signals (fourth signals) without performing signal processing as described above. It is possible to obtain RGB images with higher color reproducibility since G signals can be obtained without performing signal processing.

Sixth Embodiment

Next, a sixth embodiment of the present invention will be described. The difference between the imaging device according to the present embodiment and the imaging device 1 according to the first embodiment is the configuration of the imaging element. The difference between the imaging element 100 according to the first embodiment and an imaging element 900 according to the present embodiment is that, instead of the first pixels 103, fifth pixels 906, which output fifth signals (Y signals or yellow signals) corresponding to the exposure amount of yellow light from the incident light, are provided on a first substrate 901. Other configurations are similar to those of the first embodiment.

Each of the fifth pixels 906 may include a photodiode that detects yellow light to output a fifth signal corresponding to the exposure amount of yellow light from the incident light. Each of the fifth pixels 906 may also include a photodiode that detects light and a color filter that transmits only yellow light to output a fifth signal corresponding to the exposure amount of yellow light from the incident light.

Figure 13:
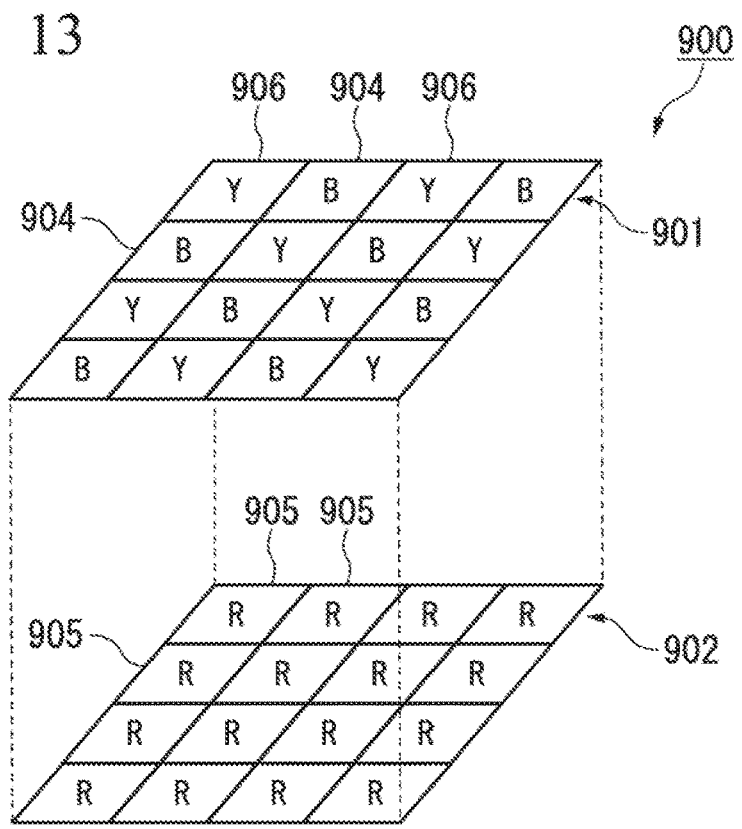
FIG. 13 is a schematic diagram showing the arrangement of second pixels, third pixels, and fifth pixels according to a sixth embodiment of the present invention.

FIG. 13 is a schematic diagram showing an arrangement of second pixels 904, third pixels 905, and fifth pixels 906 in the present embodiment. In the example shown in FIG.

13, the first substrate 901 includes eight fourth pixels 906 and eight second pixels 904 arranged regularly in a two-dimensional array of four rows and four columns. The second substrate 902 includes sixteen third pixels 905 arranged regularly in a two-dimensional array of four rows and four columns.

As shown in FIG. 13, the fifth pixels 906 and the second pixels 904 are alternately arranged on the first substrate 901. The incident light is directly incident on the fifth pixels 906 and the second pixels 904. Therefore, the first substrate 901 can output fifth signals (Y signals) corresponding to the exposure amount of yellow light from the incident light and second signals (B signals) corresponding to the exposure amount of blue light from the incident light.

The third pixels 505 are disposed on the second substrate 902. Light transmitted through the first substrate 901 among the incident light is incident on the third pixels 905. The first substrate 901 is a silicon substrate and transmits light in a wavelength bandwidth including wavelengths of red light. Thus, the second substrate 902 can output third signals (R signals) corresponding to the exposure amount of red light from the incident light.

Accordingly, with such an arrangement of the second pixels 504, the third pixels 905, and the fifth pixels 906, it is possible to simultaneously output second signals (B signals), third signals (R signals), and fifth signals (Y signals).

The respective numbers and arrangement of the fifth pixels 906 and the second pixels 904 included in the first substrate 901 and the third pixels 905 included in the second substrate 902 are not limited to those of the example shown in FIG. 13, and any respective numbers and arrangement thereof may be employed. In the example shown in FIG. 13, the third pixels 905 are disposed under the fifth pixels 906 and the second pixels 904 in correspondence therewith, but the present invention is not limited to this. For example, it is possible to design a configuration such that the pixel size of the third pixel 905 is different from the pixel size of the fifth pixel 906 and the second pixel 904 (for example, such that the pixel size of the third pixel 905 is an integer multiple of that of the fifth pixel 906).

Next, a method of generating an RGB image and an NBI image in the present embodiment will be described. The signal-processing unit 106 generates an image using a second signal, a third signal, and a fifth signal read by the signal readout unit 1025. Specifically, the signal-processing unit 106 performs calculation using the third signal (R signal) and the fifth signal (Y signal) to generate a green light signal (a G signal). Then, the signal-processing unit 106 generates an RGB image using the second signal (B signal), the third signal (R signal), and the generated green light signal (G signal). The signal-processing unit 106 generates an NBI image using the second signal (B signal).

According to the present embodiment, even when the fifth pixels 906 are provided on the first substrate 901, it is possible to simultaneously generate an RGB image and an NBI image as described above.

Seventh Embodiment

Next, a seventh embodiment of the present invention will be described. In the present embodiment, an imaging device 3000 (an endoscope-type imaging device or an endoscope apparatus) incorporating any one of the imaging elements 100, 200, 400, 600, 700, 800, and 900 described in the first to sixth embodiments will be described.

Figure 14:
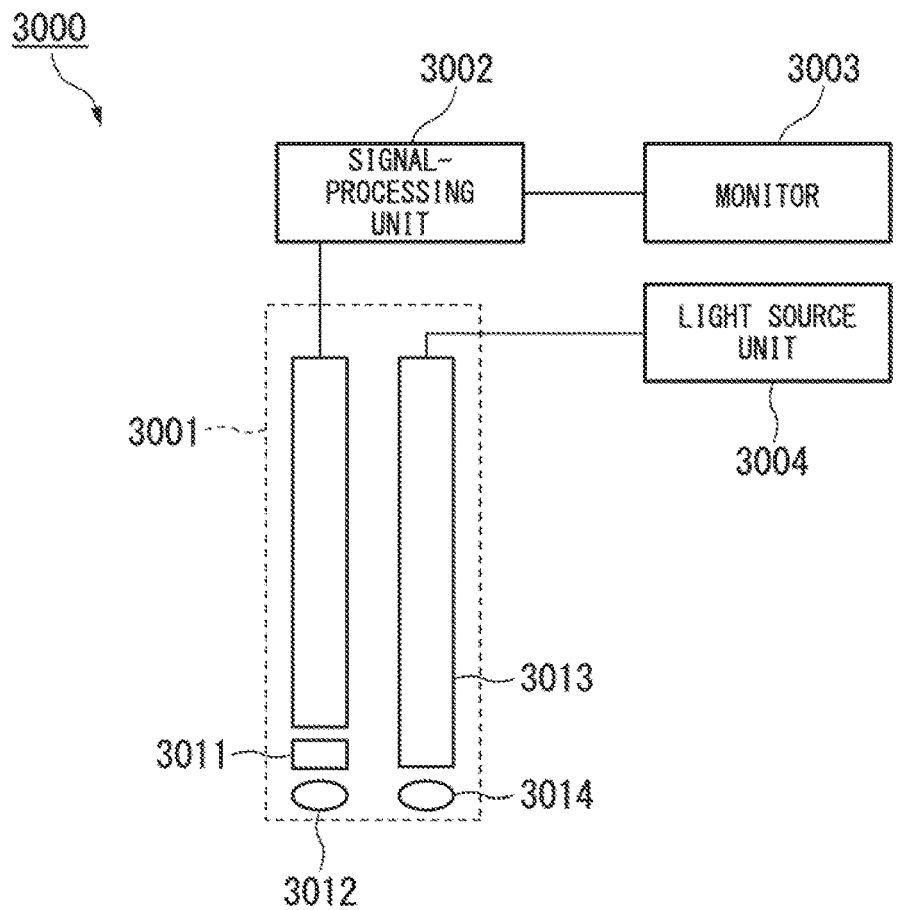
FIG. 14 is a block diagram showing a configuration of an imaging device according to a seventh embodiment of the present invention.
Figure 15:
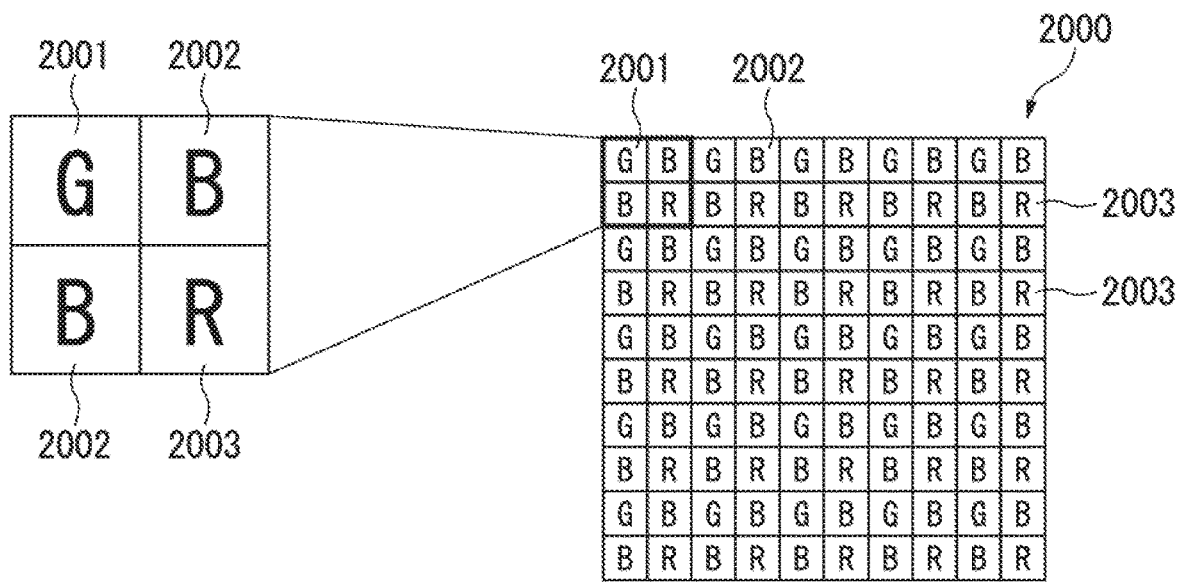
FIG. 15 is a schematic diagram, showing a pixel array of an image sensor known in the art in which the proportion of G pixels in the pixels of an image sensor having an RGB Bayer array is one pixel in every four and the proportion of B pixels is two pixels in every four.

FIG. 14 is a block diagram showing a configuration of the imaging device 3000 according to the present embodiment. In the shown example, the imaging device 3000 includes an endoscope 3001, a signal-processing unit 3002, a monitor 3003, and a light source unit 3004. The signal-processing unit 3002 generates an RGB image and an NBI image. The signal-processing unit 3002 also controls each unit of the imaging device 3000. The monitor 3003 is, for example, a liquid crystal display and displays an image. The light source unit 3004 is, for example, an LED and emits light.

The endoscope 3001 includes an imaging element 3011, an imaging lens 3012, a light guide 3013, and an illumination lens 3014. The imaging element 3011 is any one of the imaging elements 100, 200, 400, 600, 700, 800, and 900 described in the first to sixth embodiments. The imaging element 3011 is disposed at a distal end portion of the endoscope 3001. The imaging lens 3012 is disposed at the side of the light-receiving surface of the imaging element 3011. The illumination lens 3014 is disposed at a distal end portion of the light guide 3013.

The light guide 3013 emits light, generated by the light, source unit 3004 to the illumination lens 3014. The illumination lens 3014 collects the light emitted from the light guide 3013 and emits the collected light to a subject. The imaging lens 3012 collects light from the subject and emits the collected light to the imaging element 3011.

The imaging element 3011 outputs signals based on the light emitted by the imaging lens 3012. The signal-processing unit 3002 generates an RGB image and an NBI image based on the signals generated by the imaging element 3011. The method of generating an RGB image and an NBI image is similar to the method described in the first to sixth embodiments. The monitor 3003 displays the RGB image, the NBI image, or the like generated by the signal-processing unit 3002.

For example, the imaging elements 100, 200, 400, 600, 700, 800, 900 described in the first embodiment to the sixth embodiment can simultaneously capture highly accurate RGB and NBI images. Therefore, by using any one of the imaging elements 100, 200, 400, 600, 700, 800, and 900 described in the first to sixth embodiments for the imaging device 3000, it is possible to simultaneously capture highly accurate RGB and NBI images. For example, highly accurate RGB and NBI images can be used for cancer observation or the like.

For example, it is possible to more clearly observe the states of capillary vessels by irradiating the subject with narrow-band light having a center wavelength of 415 nm and a half-value width of 30 nm from the light source unit and capturing an image with the imaging device 3000.

Although preferred embodiments of the present invention have been described above, the present invention is not limited to these embodiments and modifications thereof. Additions, omissions, substitutions, and other changes of constituent elements can be made without departing from the spirit of the present invention.

The present invention is not limited by the foregoing description, but is limited only by the scope of the appended claims.

What is claimed is:

1. An imaging device, comprising:
an image sensor; and
a processor configured to process a signal output from the image sensor,
wherein the image sensor has:
a first substrate including a plurality of first pixels and a plurality of second pixels; and a second substrate including a plurality of third pixels, the second substrate facing the first substrate;

wherein the plurality of third pixels are configured to receive light transmitted through the plurality of first pixels, wherein the plurality of first pixels are configured to output signals corresponding to a wavelength bandwidth including wavelengths of green light and the plurality of first pixels are configured to transmit a wavelength bandwidth including wavelengths of red light, wherein the plurality of second pixels are configured to output signals corresponding to a wavelength bandwidth including wavelengths of blue light and not including wavelengths of red light and wavelengths of green light, wherein the plurality of third pixels are configured to output signals corresponding to a wavelength bandwidth including wavelengths of red light, wherein the plurality of first pixels and the plurality of second pixels are in correspondence with each other, and wherein the processor is configured to generate a signal at least from an output of the plurality of first pixels and an output of the plurality of third pixels, the signal corresponding to a wavelength bandwidth including wavelengths of green light and not including wavelengths of blue light and wavelengths of red light.

2. The imaging device according to claim 1, wherein a plurality of circuit regions are arranged in regions corresponding to the plurality of second pixels, and wherein the plurality of circuit regions are configured to perform at least reading of the plurality of third pixels.

3. The imaging device according to claim 2, wherein the plurality of circuit regions are configured to perform reading of the plurality of first pixels and the plurality of second pixels.

4. The imaging device according to claim 1, wherein the plurality of first pixels are configured to output signals corresponding to a wavelength bandwidth including wavelengths of green light and wavelengths of blue light.

5. The imaging device according to claim 1, wherein the plurality of first pixels are configured to output signals corresponding to a wavelength bandwidth including wavelengths of green light and not including wavelengths of blue light.

6. The imaging device according to claim 1, wherein the imaging device is configured to emit narrow-band light to highlight capillary vessels in a mucosal surface layer for observing the capillary vessels, wherein the processor is configured to generate a first image from signals output from the plurality of first pixels and the plurality of second pixels included in the first substrate, and wherein the processor is configured to generate a second image from signals output from the plurality of third pixels included in the second substrate.

7. An imaging device, comprising:

an endoscope having an imager sensor; and a processor connected to the endoscope, wherein the image sensor has:

a first substrate including a plurality of first pixels and a plurality of second pixels; and a second substrate including a plurality of third pixels, the second substrate facing the first substrate;

wherein the plurality of third pixels are configured to receive light transmitted through the plurality of first pixels, wherein the plurality of first pixels are configured to output signals corresponding to a wavelength bandwidth including wavelengths of green light and the plurality of first pixels are configured to transmit a wavelength bandwidth including wavelengths of red light, wherein the plurality of second pixels are configured to output signals corresponding to a wavelength bandwidth including wavelengths of blue light and not including wavelengths of red light and wavelengths of green light, wherein the plurality of third pixels are configured to output signals corresponding to a wavelength bandwidth including wavelengths of red light, wherein the plurality of first pixels and the plurality of second pixels are in correspondence with each other, and wherein the processor has a circuit configured to generate a signal at least from an output of the plurality of first pixels and an output of the plurality of third pixels, the signal corresponding to a wavelength bandwidth including wavelengths of green light and not including wavelengths of blue light and wavelengths of red light.

* * * * *